(12) United States Patent
Helmann

(10) Patent No.: US 6,635,475 B1
(45) Date of Patent: Oct. 21, 2003

(54) BACILLUS SUBTILIS EXTRACYTOPLASMIC FUNCTION σ FACTOR

(75) Inventor: John D. Helmann, Ithaca, NY (US)

(73) Assignee: Cornell Research Foundation, Inc., Ithaca, NY (US)

(*) Notice: Subject to any disclaimer, the term of this patent is extended or adjusted under 35 U.S.C. 154(b) by 0 days.

(21) Appl. No.: 09/627,746

(22) Filed: Jul. 28, 2000

Related U.S. Application Data

(60) Provisional application No. 60/146,466, filed on Jul. 30, 1999.

(51) Int. Cl.[7] .......................... C12N 15/63; C07H 21/04
(52) U.S. Cl. .................................... 435/320.1; 536/23.1
(58) Field of Search ....................... 435/320.1; 536/23.1

(56) References Cited

PUBLICATIONS

Jorgensen et al. Different subfamilies of alphoid repetitive DNA are present on the human and chimpanzee homologous chromosomes 21 and 22. EMBO J. vol. 6(6):1691–1696, 1987.*
Altschul, S.F., et al., *Nucleic Acids Research*, 25:3389–3402 (1997).
Asano, Y., et al., *The Journal of Biological Chemistry*, vol. 271, 47:30256–30262 (1996).
Bickel, P.E., et al., *The Journal of Biological Chemistry*, vol. 272, 21:13793–13802 (1997).
Cole, S.T., et al., *Nature*, 93:537–544 (1998).
Deuerling, E., et al., *Molecular Microbiology*, 23 (5): 921–933 (1997).
Duez, C., et al., *European Journal of Biochemistry*, 162:509–518 (1987).
Galbiati, F., et al., *Gene (Elsevier)*, 210:229–237 (1998).
Ge, Z., et al., *Journal of Bacteriology*, Nov.:6151–6157 (1996).
Helmann, J.D., *Nucelic Acids Research*, 23:2351–2360 (1995).
Honjo, M., et al., *Journal of Bacteriology*, vol. 172, 4:783–1790 (1990).
Huang, X., *Journal of Bacteriology*, vol. 179, 9:2915–2921 (1997).
Huang, X., et al., *Journal of Bacteriology*, vol. 180, 15:3765–3770 (1998).
Huang, X. et al., *Molecular Microbiology*, 31:361–371 (1999).
Huang, X., et al., *Journal of Molecular Biology*, 279:165–173 (1998).
Ichihara, S. et al., *The Journal of Biological Chemistry*, vol. 261, 20:9405–9411 (1986).
Kelly, J. A., et al., *Science*, 231:1429–1431 (1986).
Knehr, M., et al., *The Journal of Biological Chemistry*, 268:17623–17627 (1993).
Lonetto, M. A., et al., *Microbiology*, vol. 91:7573–7577 (1994).
Missiakas, D., et al., *Molecular Microbiology*, 28:1059–1066 (1998).
Moszer, I., et al., *Microbiology*, 141:261–268 (1995).
Novak, P., et al., *Journal of Bacteriology*, vol. 170, 11:5067–5075 (1988).
O'Gara, J. P., et al., *Applied and Environmental Microbiology*, vol. 63, 12:4713–4720 (1997).
Rink, R., et al., *The Journal of Biological Chemistry*, vol. 272, 23:14650–14657 (1997).
Ross., W., et al., *Science*, 262:1407–1413 (1993).
Slack, F. J., et al., *Journal of Bacteriology*, vol. 175, 15:4605–4614 (1993).
Sowell, M., O., et al., *Journal of Bacteriology*, vol. 153, 3:1331–1337 (1983).
Strauch, M. A., et al., *Molecular Microbiology*, 7:337–342 (1993).
Strauch, M. A., *Journal of Bacteriology*, vol. 177, 23:6999–7002.
Suzuki, T., et al., *Journal of Bacteriology*, vol. 169, 6:2523–2528 (1987).
Tomita, H., et al., *Journal of Bacteriology*, vol. 179, 24:7843–7855 (1997).
Uptain, S. M., et al., *Annu. Rev. Biochem.*, 66:117–72 (1997).
van Pee, K–H, *Annu. Rev. Microbiol.*, 50:375–99 (1996).
Yohda, M., et al., *The Journal of Biological Chemistry*, vol. 271, 36:22017–22021 (1996).
Zuber, P., et al., *Journal of Bacteriology*, vol. 169, 5:2223–2230 (1987).

* cited by examiner

*Primary Examiner*—Remy Yucel
*Assistant Examiner*—William Sandals
(74) *Attorney, Agent, or Firm*—Perkins, Smith & Cohen, LLP; Jacob N. Erlich; Jerry Cohen

(57) ABSTRACT

The sequences for both the sigX-dependent autoregulatory promoter, $P_X$, and the sig W-dependent autoregulatory promoter, $P_W$, are described. The protein products controlled and expressed by the $\sigma^X$ and $\sigma^W$ holoenzymes are identified, indicating that these σ factors affect responses to antimicrobial agents.

6 Claims, 7 Drawing Sheets

| Sequence | matches | located near gene | genes |
|---|---|---|---|
| (1) TGAAAC N₁₆ CGTA | 27 | 16 | see Table 1 |
| (2) TGAAAC N₁₇ CGTA | 20 | 5 | ykaB, yndN, yoaF, yoaG, yqeZ |
| (3) TGAAAC N₁₆ CGTC | 8 | 1 | asnB |
| (4) TGAAAC N₁₇ CGTC | 14 | 5 | divIC¹, ycgR², yjbC, ypuA², yrhH |
| total | 69 | 27 | |

¹These promoters are recognized by σ$^W$ and σ$^X$ in vitro (Huang, et al., 1998), and probably in vivo (Huang and Helmann, 1998).

²These putative promoters were apparently inactive when cloned at SPβ (Huang and Helmann, 1998).

FIG. 1

Alignment of σ<sup>W</sup>-like consensus elements

```
                    -30                 -10          +1
                     •                   •            •          5'-
UTR¹
sigW    aaaatTGAAACcttttgaaacgaagctCGTAtacatacaGacc              26
ydbS    aagaaTGAAACctttctgtaaaagagaCGTAtaaataaCGacg              24
yeaA    ctttaTGAAACctttggccctatttatCGTAttacgtAaaaac              24
yxjI    gagccTGAAACcttttcgccacctatcCGTAatttcatacAag              25
ysdB    aaaagTGAAACcttttctatgcttttCGTAttacatcaGAtc               30
pbpE    atattTGAAACgttagtaggttagtaaCGTAcagagatatGgg              13
yjoB    tgggaTGAAACaaaatgctatgtcaatCGTAtataacGttc                27
yteI    tgaagTGAAACatttttcatattgaatCGTAtaatgagAGaga              24
yknW    aaacaTGAAACttttgatatccttccCGTActatttgtTaga               23
ywrE    ttttaTGAAACgttttccttttcttCGTAtaaaggtaGAtt                15
yobJ    ttataTGAAACctttttattttagaaCGTAttaaaagtAaat                26
yfhL    atgcaTGAAACatttcttctttctgcaCGTAacaatgaGAagg              15
yuaF    aatttTGAAACttttcccgaggtgtctCGTAtaaatggtAacg              44
yxzE    tgaaaTGAAACcggtcagcgtttcatcCGTAtaacagatAtgg              24
yvlA    gaattTGAAACctgaagagattttaaaCGTAtaaataaGTaaa              53
xpaC    gaagaTGAAACttgtttaaggattgaaCGTAgtagataataat             (39)
CONS.        TGAAAC-ttt              CGTAtwa
```

¹The length of the 5'-untranslated region (UTR) is shown as measured from the predominant in vivo start site to the start codon of the indicated gene. The value for *xpaC* is shown in parenthesis since this putative promoter has not been detected by primer extension experiments. The start sites for *yobJ, yxzE,* and *yvlA* were determined using a non-cognate sequencing ladder and are therefore marginally less precise than those for other genes.

FIG. 2

| Protein | AA | Loc. | Known or putative function | Homology (characterized protein of highest identity, or closest paralogues) | Ident. | v |
|---|---|---|---|---|---|---|
| SigW | 187 | C | σ factor | P.aeruginosa AlgU (AlgT) | 37% 69/183 | 6 |
|  |  |  |  | M. tuberculosis SigE | 35% 61/171 | 3 |
| -YbbM | 208 | M | anti-σ | Bsu YlaD | 34% 17/50 | 8 |
| YdbS | 159 | M | Unknown | Mtb hypothetical protein MTCI61.10c. | 27% 33/118 | 3 |
| -YdbT | 493 | M | Unknown | Bsu YdbS (one domain) | 22% 22/98 |  |
| YeaA | 329 | C | Unknown | none |  |  |
| -YdjP | 271 | M | peroxidase | Str. aureofaciens bromoperoxidase | 26% 75/281 | 7 |
|  |  |  |  | Bsu YisY | 25% 67/265 | 4 |
| -YdjO | 69 |  | Unknown | none |  |  |
| YxjI | 162 | M | Unknown | none |  |  |
| YsdB | 130 | M | Unknown | none |  |  |
| PbpE | 451 | M | PBP4* | B. cereus, alkaline D-peptidase | 28% 84/300 | 2 |
|  |  |  |  | Str.lividans D-ala, D-ala carboxypeptidase | 23% 85/356 | 8 |
|  |  |  |  | Str. sp. D-ala, D-ala carboxypeptidase | 24% 83/340 | 3 |
| -RacX | 227 |  | aspartate racemase | Desulfurococcus Asp racemase | 28% 66/233 | 2 |
| YjoB | 423 | ? | Unknown | Helicobacter pylori FtsH homolog; AAA motif (ftsH-like) CDC48 family | 28% 81/286 | 1 |
| YknW | 231 | M | Unknown | none |  |  |
| -YknX | 377 | M | ABC transporter | Bsu YvrP | 30% 103/335 | 3 |
|  |  |  |  | Streptococcus crista TptB | 25% 90/360 | 2 |
|  |  |  |  | Enterococcus faecalis BacG | 22% 83/376 | 4 |
| -YknY | 230 | M | ABC transporter (ATP-binding protein) | Bsu YvrO | 61% 140/227 | 2 |
|  |  |  |  | Streptococcus crista TptC | 55% 125/224 | 1 |
|  |  |  |  | Enterococcus faecalis BacH | 48% 90/187 | 3 |
| -YknZ | 397 | M | ABC transporter | Bsu YvrN | 34% 143/410 | 4 |
|  |  |  |  | Streptococcus crista TptD | 30% 94/311 | 2 |
|  |  |  |  | Enterococcus faecalis BacI | 25% 101/404 | 4 |
| YteI | 335 | M | protease IV | E. coli protease IV (SppA) | 34% 74/213 | 4 |
| -YteJ | 164 | M | Unknown | Vibrio cholerae OrfY | 33% 46/139 | 2 |
|  |  |  |  | Bsu YxaI | 27% 43/154 | 4 |
| YuaF | 174 | M | Unknown | none |  |  |
| -YuaG | 509 | M | Unknown | Drosophila melanogaster Flotillin-1 | 36% 162/449 | 1 |
| -YuaI | 173 |  | Unknown | Bsu PaiA | 23% 33/141 | 1 |
| YwrE | 111 | M | Unknown | none |  |  |
| YfhL | 110 | M | Unknown | none |  |  |
| -YfhM | 286 | C | epoxide hydrolase | Rat soluble epoxide hydrolase | 30% 94/309 | 3 |
|  |  |  |  | M. tuberculosis Rv3617 | 38% 67/173 | 3 |
| YobJ | 280 | M | Unknown | none |  |  |
| XpaC | 204 | S | Unknown | none |  |  |
| -YaaN | 386 |  | Unknown | R. sphaeroides tellurite resistance protein | 33% 115/346 | 9 |
|  |  |  |  | Bsu YceH | 27% 97/347 | 4 |
| YvlA | 108 | M | Unknown | none |  |  |
| -YvlB | 365 | C | Unknown | none |  |  |
| -YvlC | 65 | M | Unknown | E. coli phage shock protein C | 33% 18/54 | 4 |
| -YvlD | 119 | M | Unknown | M. leprae putative membrane protein | 45% 28/61 | 6 |
| YxzE | 66 | M | Unknown | none |  |  |

FIG. 3

Expression of P-*lacZ* fusions in vivo

| Strain d fusion f | wt[1] | SigW | sigX | sigY | rsiX | wt | sigW |
|---|---|---|---|---|---|---|---|
| | | | | | | Miller units[2] | |
| SigW | ++ | - | +++ | ++ | + | 56 | 0.9 |
| YdbS | ++ | - | +++ | ++ | + | 48 | 0.7 |
| YeaA | + | - | ++ | + | +/- | 19 | 0.9 |
| YxjI | + | - | ++ | + | +/- | 5.3 | 0.3 |
| YsdB | + | - | ++ | + | +/- | 4.6 | 0.6 |
| PbpE | + | - | ++ | + | +/- | 16 | 0.7 |
| YjoB | + | - | ++ | +++ | +/- | 8.7 | 0.4 |
| YteI | + | - | ++ | + | +/- | 6.8 | 0.7 |
| YknW | ++ | + | +++ | ++ | + | 41 | 5.3 |
| YuaF | + | - | ++ | + | +/- | 2.6 | 0.5 |
| YfhL | + | - | ++ | + | +/- | 2.4 | 0.5 |
| YwrE | +/- | - | + | - | - | 2.0 | 0.5 |
| YobJ | + | - | nd[3] | nd | nd | 11 | 0.5 |
| XpaC | + | + | nd | nd | nd | 4.3 | 3.4 |
| YvlA | + | - | nd | nd | nd | 3.6 | 1.2 |
| YxzE | +/- | - | nd | nd | nd | 1.7 | 0.6 |

[1] Expression of each gene was measured by growth on sporulation plates containing 2% glucose and X-gal. Colony color was observed after 1-3 days: +++ (strong blue) > ++ (blue) > + (light blue) > +/- (very light blue) > - (white after one week).

[2] β-galactosidase assays were performed after growth in 4xSG medium to approximately $T_2$. All values are rounded to 2 significant figures and are averages from two or more cultures.

[3] nd; not done

SEQUENCE LISTING

<160> NUMBER OF SEQ ID NOS: 21

<210> SEQ ID NO 1
<211> LENGTH: 26
<212> TYPE: DNA
<213> ORGANISM: Sigma Factor Consensus Sequence
<220> FEATURE:
<221> NAME/KEY: misc_feature
<223> OTHER INFORMATION: "n" is defined as any nucleotide

<400> SEQUENCE: 1
tgaaacnnnn nnnnnnnnnn nncgta                                    26

<210> SEQ ID NO 2
<211> LENGTH: 27
<212> TYPE: DNA
<213> ORGANISM: Sigma Factor Consensus Sequence
<220> FEATURE:
<221> NAME/KEY: misc_feature
<223> OTHER INFORMATION: "n" is defined as any nucleotide

<400> SEQUENCE: 2
tgtaacnnnn nnnnnnnnnn nnncgac                                   27

```
<210> SEQ ID NO 3
<211> LENGTH: 27
<212> TYPE: DNA
<213> ORGANISM: Bacillus subtilis
<220> FEATURE:
<221> NAME/KEY: misc_feature
<223> OTHER INFORMATION: "n" is defined as any nucleotide

<400> SEQUENCE: 3
tgaaacnnnn nnnnnnnnnn nnncgta                                27

<210> SEQ ID NO 4
<211> LENGTH: 26
<212> TYPE: DNA
<213> ORGANISM: Bacillus subtilis
<220> FEATURE:
<221> NAME/KEY: misc_feature
<223> OTHER INFORMATION: "n" is defined as any nucleotide

<400> SEQUENCE: 4
tgaaacnnnn nnnnnnnnn nncgtc                                  26

<210> SEQ ID NO 5
<211> LENGTH: 27
<212> TYPE: DNA
<213> ORGANISM: Bacillus subtilis
<220> FEATURE:
<221> NAME/KEY: misc_feature
<223> OTHER INFORMATION: "n" is defined as any nucleotide

<400> SEQUENCE: 5
tgaaacnnnn nnnnnnnnnn nnncgtc                                27

<210> SEQ ID NO 6
<211> LENGTH: 43
<212> TYPE: DNA
<213> ORGANISM: Bacillus subtilis

<400> SEQUENCE: 6
aaaattgaaa cctttttgaaa cgaagctcgt atacatacag acc             43

<210> SEQ ID NO 7
<211> LENGTH: 43
<212> TYPE: DNA
<213> ORGANISM: Bacillus subtilis

<400> SEQUENCE: 7
aagaatgaaa cctttctgta aaagagacgt ataaataacg acg              43

<210> SEQ ID NO 8
<211> LENGTH: 43
<212> TYPE: DNA
<213> ORGANISM: Bacillus subtilis

<400> SEQUENCE: 8
ctttatgaaa cctttggccc tatttatcgt attacgtaaa aac              43

<210> SEQ ID NO 9
<211> LENGTH: 43
<212> TYPE: DNA
<213> ORGANISM: Bacillus subtilis

<400> SEQUENCE: 9
gagcctgaaa cctttttcgcc acctatccgt aatttcatac aag             43
```

-continued

```
<210> SEQ ID NO 10
<211> LENGTH: 43
<212> TYPE: DNA
<213> ORGANISM: Bacillus subtilis

<400> SEQUENCE: 10
aaaagtgaaa ccttttctta tgcttttcgt attacatcag atc            43

<210> SEQ ID NO 11
<211> LENGTH: 43
<212> TYPE: DNA
<213> ORGANISM: Bacillus subtilis

<400> SEQUENCE: 11
atatttgaaa cgttagtagg ttagtaacgt acagagatat ggg            43

<210> SEQ ID NO 12
<211> LENGTH: 43
<212> TYPE: DNA
<213> ORGANISM: Bacillus subtilis

<400> SEQUENCE: 12
tgggatgaaa caaaatgcta tgtcaatcgt atatataacg ttc            43

<210> SEQ ID NO 13
<211> LENGTH: 43
<212> TYPE: DNA
<213> ORGANISM: Bacillus subtilis

<400> SEQUENCE: 13
tgaagtgaaa catttttcat attgaatcgt ataatgagag aga            43

<210> SEQ ID NO 14
<211> LENGTH: 43
<212> TYPE: DNA
<213> ORGANISM: Bacillus subtilis

<400> SEQUENCE: 14
aaacatgaaa cttttgata tccttcccgt actatttgtt aga             43

<210> SEQ ID NO 15
<211> LENGTH: 43
<212> TYPE: DNA
<213> ORGANISM: Bacillus subtilis

<400> SEQUENCE: 15
ttttatgaaa cgttttcct tttcttcgt ataaaggtag att               43

<210> SEQ ID NO 16
<211> LENGTH: 43
<212> TYPE: DNA
<213> ORGANISM: Bacillus subtilis

<400> SEQUENCE: 16
ttatatgaaa ccttttttat tttagaacgt attaaaagta aat             43

<210> SEQ ID NO 17
<211> LENGTH: 43
<212> TYPE: DNA
<213> ORGANISM: Bacillus subtilis

<400> SEQUENCE: 17
atgcatgaaa catttcttct ttctgcacgt aacaatgaga agg             43
```

```
<210> SEQ ID NO 18
<211> LENGTH: 43
<212> TYPE: DNA
<213> ORGANISM: Bacillus subtilis

<400> SEQUENCE: 18
aattttgaaa cttttcccga ggtgtctcgt ataaatggta acg                43

<210> SEQ ID NO 19
<211> LENGTH: 43
<212> TYPE: DNA
<213> ORGANISM: Bacillus subtilis

<400> SEQUENCE: 19
tgaaatgaaa ccggtcagcg tttcatccgt ataacagata tgg                43

<210> SEQ ID NO 20
<211> LENGTH: 43
<212> TYPE: DNA
<213> ORGANISM: Bacillus subtilis

<400> SEQUENCE: 20
gaatttgaaa cctgaagaga ttttaaacgt ataaataagt aaa                43

<210> SEQ ID NO 21
<211> LENGTH: 43
<212> TYPE: DNA
<213> ORGANISM: Bacillus subtilis

<400> SEQUENCE: 21
gaagatgaaa cttgtttaag gattgaacgt agtagataat aat                43
```

BACILLUS SUBTILIS EXTRACYTOPLASMIC FUNCTION σ FACTOR

This application claims priority of U.S. Provisional Application Ser. No. 60/146,466 filed Jul. 30, 1999 entitled BACILLUS SUBTILIS EXTRACYTOPLASMIC FUNCTION SIGMA FACTOR.

STATEMENT OF GOVERNMENT INTEREST

This invention was made with Government support under Grant No. GM-47446, awarded by the National Institutes of Health. The United States Government has certain rights in this invention.

FIELD OF THE INVENTION

This invention relates to Bacillus subtilis extracytoplasmic function (ECF) σ factors and their function as well as to their encoding and regulatory gene sequences.

BACKGROUND OF THE INVENTION

The extracytoplasmic function (ECF) subfamily of σ factors are a structurally distinct group of proteins that control a great variety of functions often involving the secretion or uptake of macromolecules or ions in both Grain-negative and Gram-positive bacteria (Lonetto, M. A., Brown, K. L., Rudd, K. E. and Buttner, M. J. (1994) Analysis of the Streptomyces coelicolor sigE gene reveals the existence of a subfamily of eubacterial σ factors involved in the regulation of extracytoplasmic functions. Proc Natl Acad Sci USA 91:7573–7577; Missiakas, D. and Raina, S. (1998) The extracytoplasmic function sigma factors: role and regulation. Molecular Microbiology 28:1059–1066). Well-characterized examples include E. coli RpoE ($\sigma^E$) and FecI and Pseudomonas aeruginosa AlgU. Whole bacterial genome sequencing has revealed numerous new members of this class and suggests the presence of seven σ factors in Bacillus subtilis (Kunst, F., Ogaswara, N., Moszer, I., Albertini, A. M., Alloni, G., Azevedo, A., et al. (1997) The complete genome sequence of the Gram-positive bacterium Bacillus subtilis. Nature 390:249–256) and ten in Mycobacterium tuberculosis (Cole, S. T., Brosch, R., Parkhill, J., Gamier, T., Churcher, C., Harris, D., et al. (1998) Deciphering the biology of Mycobacterium tuberculosis from the complete genome sequence. Nature 393:537–544). The roles of the B. subtilis ECF σ factors are largely unexplored, and it is not known whether they control distinct or overlapping sets of genes. None of the ECF σ factors in B. subtilis correspond to known regulatory loci despite extensive genetic analysis of this organism. This suggests that the functions controlled by these proteins are not relevant in standard laboratory culture conditions, that the σ factors are redundant in function, or both.

The roles of two ECF σ factors, $\sigma^X$ and $\sigma^W$, have been identified by a combination of gene disruption and target promoter identification. It has been found that $\sigma^X$ and $\sigma^W$ activate partially overlapping sets of genes that are optimally transcribed in late logarithmic and early stationary phase, respectively (Huang, X., Fredrick, K. L. and Helmann, J. D. (1998) Promoter recognition by Bacillus subtilis $\sigma^W$: Autoregulation and partial overlap with the $\sigma^X$ regulon. J Bacteriol 180:3765–3770). One sigX mutant displays a slightly increased sensitivity to heat and oxidative stresses, but has no other obvious phenotypes (Huang, X., Decatur, A., Sorokin, A. and Helmann, J. D. (1997) The Bacillus subtilis $\sigma^X$ protein is an extracytoplasmic function sigma factor contributing to the survival of high temperature stress. J Bacteriol 179:2915–2921).

The fact that many ECF σ factors regulate their own expression can be used to determine the role of each ECF σ. The sequence of the autoregulatory promoter site can be used to identify related sequences in the genome that potentially control the transcription of target genes. The sigX operon is preceded by an autoregulatory promoter element, $P_X$, that is exclusively dependent on sigX in vivo (Huang et al., 1997). Like sigX, the sigW gene is autoregulated (Huang et al., 1998). Overproduction of $\sigma^W$ and reconstitution of $\sigma^W$ holoenzyme (E$\sigma^W$) indicate that E$\sigma^W$ recognizes a subset of $\sigma^W$-dependent promoters in vitro, including abh, divIC, yrhH and ywbN (Huang et al., 1998). Indeed, each of these four promoters is active in a sigX mutant strain and, for the latter two, the corresponding transcripts are missing in a sigX sigW double mutant (Huang and Helmann, 1998).

Identification of the promoter sequences recognized by $\sigma^X$ and $\sigma^W$ can lead to their use in a variety of assays to identify substances that can modulate bacterial growth and replication.

SUMMARY OF THE INVENTION

The sigX operon is preceded by an autoregulatory promoter element, $P_X$, that is exclusively dependent on sigX in vivo (Huang et al., 1997). By saturation mutagenesis, the 10 bases most critical for recognition of $P_X$ in vivo have been identified. By using this experimentally derived consensus sequence, 10 putative $\sigma^X$-dependent promoter elements from the B. subtilis genome have been tested and identified (Huang, X. and Helmann, J. D. (1998) Identification of target promoters for the Bacillus subtilis $\sigma^X$ factor using a consensus-directed search. J Mol Biol 279:165–173).

Of the ten putative $\sigma^X$-dependent promoters, at least seven are active in vivo and three (csbB, lytR, rapD) are completely dependent on $\sigma^X$ for expression. However, for these three genes, an additional $\sigma^X$-independent promoter also contributes to expression. Since lytR regulates autolysin expression and csbB encodes a putative membrane bound glycosyl transferase, the $\sigma^X$ regulon may act to modify the cell wall during the transition to a non-growing state (Huang and Helmann, 1998). The four remaining active promoters are partially dependent on the holoenzyme, E$\sigma^X$, but are also recognized by one or more other forms of holoenzyme (including E$\sigma^W$). However, since most genes of the sigX regulon can be transcribed by multiple holoenzymes, a sigX mutation is unlikely to abolish gene expression. This may account, in part, for the lack of an obvious phenotype for a sigX mutant.

The Bacillus subtilis sigW gene encodes an extracytoplasmic function (ECF) σ factor that is expressed in early stationary phase from a sigW-dependent autoregulatory promoter, $P_W$. Using a consensus-based search procedure, fifteen operons preceded by promoters similar in sequence to $P_W$ were identified. At least fourteen of these promoters are dependent on $\sigma^W$ both in vivo and in vitro as judged by lacZ reporter fusions, run-off transcription assays, and nucleotide resolution start site mapping. Thus, $\sigma^W$ controls a regulon of more than 30 genes, many of which encode membrane proteins of unknown function. The $\sigma^W$ regulon includes a penicillin-binding protein (PBP4*) and a co-transcribed amino acid racemase (RacX), homologs of signal peptide peptidase (YteI), flotillin (YuaG), ABC transporters (YknXYZ), non-heme bromoperoxidase (YdjP), epoxide hydrolase (YfhM), and three small peptides with structural similarities to bacteriocin precursor polypeptides.

Therefore, $\sigma^W$ activates a large stationary phase regulon that functions in detoxification, production of antimicrobial compounds, or both. The $\sigma^W$ regulon and its products can be used to develop expression vector systems that can be used for screening assays to identify new, and potentially efficacious antibacterial agents.

Other objects, features, and advantages will be apparent from the following detailed description of preferred embodiments taken in conjunction with the accompanying drawings in which:

BRIEF DESCRIPTION OF THE DRAWINGS

FIG. 1 shows the occurrence of sequences similar to $P_W$ in the B. subtilis genome. Note that (1) indicates SEQ ID NO: 1, (2) indicates SEQ ID NO: 3, (3) indicates SEQ ID NO: 4, and (4) indicates SEQ ID) NO: 5.

FIG. 2 shows the alignment of $\sigma^W$-like consensus elements. Note that sigW indicates SEQ ID NO: 6, ydbS indicates SEQ ID NO: 7, yeaA indicates SEQ ID NO: 8, yxjI indicates SEQ ED NO: 9, ysdB indicates SEQ ID NO: 10, pbpE indicates SEQ ID NO: 11, yjoB indicates SEQ ID NO: 12, yteI indicates SEQ ID NO: 13, yknW indicates SEQ ID NO: 14, ywrE indicates SEQ ID NO: 15, yobJ indicates SEQ ID NO: 16, yjhL indicates SEQ ID NO: 17, yuaF indicates SEQ ID NO: 18, yxzE indicates SEQ ID NO: 19, yvlA indicates SEQ ID NO: 20, and xpaC indicates SEQ ID NO: 21.

FIG. 3 shows the $\sigma^W$ regulon.

FIG. 5 shows the expression of P-lacZ fusions in vivo.

DETAILED DESCRIPTION OF PREFERRED EMBODIMENTS

Figure 4:
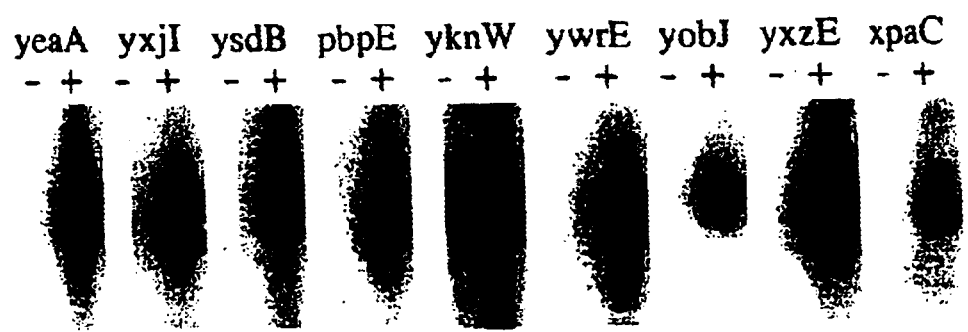
FIG. 4 shows the in vitro recognition of predicted $\sigma^W$-dependent promoters. PCR products containing the indicated promoter regions were incubated with B. subtilis RNAP in the absence (−) or presence (+) of purified $\sigma^W$ and run-off transcription products were visualized by autoradiography. In all cases, the observed sizes of the run-off products are consistent with the transcription start points assigned by primer extension mapping.

Based on a comparison of promoter sequences, $E\sigma^W$ preferentially recognizes promoters with a −10 consensus element of CGTN while $E\sigma^X$ prefers CGNC (where N is not absolutely specified). Thus, promoters that have a −10 element of CGTC can be recognized by both holoenzymes.

The sigX operon is preceded by an autoregulatory promoter element, $P_X$, that is exclusively dependent on sigX in vivo (Huang et al., 1997). By saturation mutagenesis, the 10 bases most critical for promoter recognition in vivo have been identified. By using this experimentally derived consensus sequence, 10 putative $\sigma^X$-dependent promoter elements from the B. subtilis genome have been tested and identified (Huang, X. and Helmann, J. D. (1998) Identification of target promoters for the Bacillus subtilis $\sigma^X$ factor using a consensus-directed search. J Mol Biol 279:165–173).

Of the ten putative $\sigma^X$-dependent promoters, at least seven are active in vivo and three (csbB, lytR, rapD) are completely dependent on $\sigma^X$ for expression. However, for these three genes, an additional $\sigma^X$-independent promoter also contributes to expression. Since lytR regulates autolysin expression and csbB encodes a putative membrane bound glycosyl transferase, the $\sigma^X$ regulon may act to modify the cell wall during the transition to a non-growing state (Huang and Helmann, 1998). The four remaining active promoters are partially dependent on the holoenzyme, $E\sigma^X$, but are also recognized by one or more other forms of holoenzyme (including $E\sigma^W$). However, since most genes of the sigX regulon can be transcribed by multiple holoenzymes, a sigX mutation is unlikely to abolish gene expression. This may account, in part, for the lack of an obvious phenotype for a sigX mutant.

Computer-aided genome analysis was used to help identify $\sigma^W$-dependent promoters. The sigW gene is positively autoregulated from a $\sigma^W$-dependent promoter element ($P_W$) activated during early stationary phase (Huang et al., 1998). $P_W$ (SEQ ID NO: 1) was originally detected as a sequence similar to the $\sigma^X$-dependent autoregulatory site, $P_X$ (SEQ ID NO: 2). Despite their considerable sequence similarity, $P_W$ is recognized by $E\sigma^W$, but not by $E\sigma^X$, both in vivo and in vitro. Similarly, $P_X$ is recognized by $E\sigma^X$, but not by $E\sigma^W$. Thus, the $\sigma^X$ and $\sigma^W$ holoenzymnes have distinct promoter selectivities.

In addition to $P_W$, $\sigma^W$ recognizes a subset of promoters identified as part of the $\sigma^X$ regulon (Huang et al., 1998). Based on promoter sequence comparisons, it appeared that $\sigma^W$ would recognize promoters containing a −35 consensus element (TGAAAC), a spacer of either 16 or 17 basepairs, and a −10 consensus element of CGT(A or C). A summary of sequences matching these patterns, both in the whole B. subtilis genome and located upstream of assigned reading frames, is presented in FIG. 2. Only those elements matching $P_W$ both in spacer length and at all ten consensus positions (group 1) were investigated. These are likely to represent only a subset of $\sigma^W$-dependent promoter sites and it is possible that the sequences in groups 2 and 3 are also recognized by $\sigma^W$. As noted above, at least two of the group 4 promoters are also recognized by $\sigma^W$. In addition, previous analyses have suggested that $\sigma^W$ can tolerate some deviation from consensus in the −35 element (e.g. abh and ywbN), making the pool of potential promoter sites even larger.

Thus, $\sigma^W$ controls a large regulon of genes expressed in stationary phase. This contrasts sharply with other characterized ECF σ factors. In general, regulons controlled by ECF σ factors seem to be quite small, involving at most a few target promoter elements. For example, a recent review lists a total of 8 identified proteins that are under direct control of E. coli $\sigma^E$ (Missiakas and Raina, 1998).

The sequence characteristics of $\sigma^W$-dependent promoters were determined using 10-basepair search strings. This choice was based largely on knowledge of the positions that are important for function as judged by mutagenesis of the similar $\sigma^X$-dependent $P_X$ element (Huang and Helmann, 1998), and does not necessarily include all the sequence information relevant for site selection. In general, a unique 10 basepair sequence is expected to occur by chance between 8 and 10 times (depending on AT content) in the 4.2 Mb *B. subtilis* genome. This presumably explains the difference between the total number of observed matches (69) and those either shown or suspected to be functionally important (27) as described in FIG. 1.

The mechanisms by which RNAP discriminates between functional promoters and non-functional sites of the same sequence are not clear. Other DNA features important for promoter selectivity include T-tracts in the spacer region (11 of the 15 promoters have at least three T residues in a row), and sequences just downstream of the −10 CGTA element (half of the group 1 promoters have the extended −10 sequence CGTATA; FIG. 2). Finally, the region between −40 and −65 in bacterial promoters is clearly non-random. In a compilation of promoters recognized by $\sigma^A$ RNAP, a distinct alternating pattern of A- and T-rich regions was observed (Helmann, J. D. (1995) Compilation and analysis of *Bacillus subtilis* $\sigma^X$-dependent promoter sequences: Evidence for extended contact between RNA polymerase and upstream promoter DNA. *Nucleic Acids Res* 23:2351–2360). These sequences are similar to upstream promoter (UP) elements that function by interaction with the a subunits of RNAP (Ross, W., Gosink, K. K., Salomon, J., Igarishi, K., Zou, C., Ishiharna, A., Severinov, K. and Gourse, R. L. (1993) A third recognition element in bacterial promoters: DNA binding by the σ subunit of RNA polymerase. *Science* 262:1407–1413) and may also facilitate the wrapping of promoter region DNA around RNAP. Sequences that are likely to function as UP elements are found upstream of several of the $\sigma^W$-dependent promoters and presumably also play a role in site selection.

The prediction of promoter sites using DNA sequence information is far from an exact science. The most thoroughly studied class of bacterial promoters is that recognized by *E. coli* $\sigma^{70}$. However, as a class these are quite difficult to accurately predict using weight matrix methods without a high frequency of false-positives (Hertz, G. Z. and Stormo, G. D. (1996) *Escherichia coli* promoter sequences: analysis and prediction in *Methods in Enzymology*. Adhya, S. (eds). San Diego, Calif., Academic Press, pp 30–42). This difficulty is due to a relatively low level of sequence conservation, which is postulated to reflect the presence of a large fraction of sites that require a positive activator for function (Hertz and Stormo, 1996). Computer-aided definition of regulons controlled by ECF σ factors may benefit from a higher level of sequence conservation. Promoters controlled by ECF σ factors are often controlled by a ligand-responsive σ-anti-σ interaction, rather than by a requirement for a positive activator. In addition, the presence of several ECF σ factors in the same bacterium may provide selection for a high level of sequence conservation within each distinct class of elements, despite similarities in the −35 recognition regions. These two factors may combine to produce a set of highly conserved elements suitable for detection by computer analysis.

The identification of 15 new promoter elements indicates that $\sigma^W$ controls the transcription of at least 32 gene products, many of unknown function (FIG. 3). Despite the size of the $\sigma^W$ regulon, a sigW mutant does not display any gross phenotypic abnormalities. For example, a sigW mutant strain is unaffected in sporulation, the development of competence, or protein secretion, all events normally associated with post-exponential phase.

The only members of the regulon that have been previously studied are pbpE and a cotranscribed gene postulated to encode an amino acid racemase (Popham, D. L. and Setlow, P. (1993) Cloning, nucleotide sequence, and regulation of the *Bacillus subtilis* pbpE operon, which codes for penicillin-binding protein 4* and an apparent amino acid racemase. *J Bacteriol* 175:2917–2925). However, mutation of either or both of these genes does not confer a detectable phenotype. PBP4*, encoded by pbpE, was originally identified as a penicillin-binding protein induced during sporulation and absent from a spo0A mutant strain (Sowell, M. O. and Buchanan, C. E. (1983) Changes in penicillin-binding proteins during sporulation of *Bacillus subtilis*. *J Bacteriol* 153:1331–1337). Thus, PBP4* was postulated to be associated with sporulation, although the absence of PBP4* from some strains raised doubts as to whether this protein was essential for sporulation (Sowell and Buchanan, 1983). The effects of the spo0A mutation on pbpE synthesis can be suppressed by an abrB mutation (Popham and Setlow, 1993) and AbrB has been shown to bind to the pbpE promoter region (Strauch, M. A. (1995) Delineation of AbrB-binding sites on the *Bacillus subtilis* spo0H, kinB, ftsAZ and pbpE promoters and use of a derived homology to identify a previously unsuspected binding site in the bsuBI methylase promoter. *J Bacteriol* 177:6999–7002). Since abrB mutations suppress several of the pleiotropic phenotypes of a spo0A mutation (Strauch, M. A. and Hoch, J. A. (1993) Transition-state regulators: sentinels of *Bacillus subtilis* post-exponential gene expression. *Mol Microbiol* 7:337–342), but do not restore sporulation, it is clear that PBP4* synthesis can be uncoupled from the sporulation process. Thus, there is no currently no evidence that PBP4* has a role specific for, or even related to, sporulation.

Several additional members of the $\sigma^W$ regulon are related to proteins, or families of proteins, from other organisms (FIG. 3). These include YjoB, containing an AAA motif characteristic of FtsH family proteins. The AAA motif is a 230 amino acid region identified in a large number of proteins of diverse function, hence the acronym for ATPase-Associated with a variety of cellular Activities (Confalonieri, F. and Duguet, M. (1995) A 200-amino acid ATPase module in search of a basic function. *BioEssays* 17:639–650). YteI is the *B. subtilis* homolog of signal peptide peptidase (protease IV), a membrane bound protease that degrades signal peptides after their removal by signal peptidases (Novak, P. and Dev, I. K. (1988) Degradation of signal peptide by protease IV and oligopeptidase A. *J Bacteriol* 170:5067–5075; Suzuki, T., A. Itoh, lehihara, S. and Mizushima, S. (1987) Characterization of three sppA gene coding for protease IV, a signal peptide peptidase of *Escherichia coli*. *J Bacteriol* 169:2523–2528). YuaG is related to flotillin, which together with epidermal surface antigen, defines a family of conserved integral membrane proteins of unknown function (Bickel, P. E., Scherer, P. E., Schnitzer, J. E., Oh, P., Lisanti, M. P. and Lodish, H. F. (1997) Flotillin and epidermal surface antigen define a new family of caveolae-associated integral membrane protein. *J Biol Chem* 272:13793–13802). YuaI is related to a *B. subtilis* protein, PaiA, postulated to be a transcriptional regulator affecting protein secretion (Honjo, M., Nakayama, A., Fukazawa, K., Kawamura, K., Ando, K., Hori, M. and Furutani, Y. (1990) A novel *Bacillus subtilis* gene involved in negative control of sporulation and degradative-enzyme production. *J Bacteriol* 172:1783–1790).

Several members of the $\sigma^W$ regulon may play a role in detoxification. YdjP is a member of the non-heme bromoperoxidase family of proteins (Hecht, H. J., Sobek, H., Haag, T., Pfeifer, O. and van Pee, K. H. (1994) The metal-ion-free oxidoreductase from *Streptomyces aureofaciens* has an alpha-beta hydrolase fold. *Nature Structural Biology*

1:532–537; Pelletier, I., Pfeifer, O., Aftenbuchner, J. and van Pee, K. H. (1994) Cloning of a second non-haem bromoperoxidase gene from *Streptomyces aureofaciens* ATCC 10762: sequence analysis, expression in *Streptomyces lividans* and enzyme purification. *Microbiology* 140:509–516) and YfhM is related to mammalian and microbial epoxide hydrolases (Rink, R., Fennema, M., Smids, M., Dehmel, U. and Janssen, D. B. (1997) Primary structure and catalytic mechanism of the epoxide hydrolase from *Agrobacterium radiobacter* AD1. *J Biol Chem* 272:14650–14657). These two classes of enzymes appear to be structurally related because both have an α/β hydrolase fold and a conserved catalytic triad. The functions of microbial non-heme haloperoxidases are unclear. These enzymes seem to have broad substrate specificity and attempts to link them to the synthesis of halogenated secondary metabolites, including many antibiotics, have been generally unsuccessful (van Pee, K. H. (1996) Biosynthesis of halogenated metabolites by bacteria. *Ann Rev Microbiol* 50:375–399). Although epoxide hydrolases are of interest for their utility in the enantioselective resolution of racemic epoxide mixtures (Finney, N. S. (1998) Enantioselective epoxide hydrolysis: catalysis involving microbes, mammals and metals. *Chemistry & Biology* 5: R73–R79), their physiological roles are not well defined. Since epoxides are reactive functional groups found in several antimicrobials (Bugg, T. D. H. and Walsh, C. T. (1993) Intracellular steps of bacterial cell wall peptidoglycan biosynthesis: enzymology, antibiotics, and antibiotic resistance. *Nat Prod Rep* 9:199–215; Zuber, P., Nakano, M. M. and Marehiel, M. A. (1993) Peptide antibiotics. In *Bacillus subtilis* and other Gram-positive bacteria. Sonenshein, A. L., Hoch, J. A. and Losick, R. (eds.), Washington, D.C., ASM Press, pp 897–916), including bacilysin, a role for YfhM in detoxification is suggested. Further support for this notion is provided by the recent finding that yndN (FIG. 1, group 2) is also part of the $\sigma^W$ regulon and encodes a fosfomycin resistance protein.

Other members of the $\sigma^W$ regulon may be involved in bacteriocin production or secretion. Three members of the $\sigma^W$ regulon (ydjO, yviC, and yxzE) encode small hydrophobic proteins reminiscent of bacteriocin precursor polypeptides (Jack, R. W., Tagg, J. R. and Ray, B. (1995) Bacteriocins of Gram-positive bacteria. *Microbiol Rev* 59:171–200). Both YdjO and YxzE are rich in cysteine, serine, and threonine which are amino acids involved in the post-translational modifications characteristic of antibiotics. In fact, the yknW operon encodes an ATP-binding cassette (ABC) transporter closely related to an *Enterococcus faecalis* transporter that functions in bacteriocin export (Tomita, H., Fujimoto, S., Tanimoto, K. and Ike, Y. (1997) Cloning and genetic and sequence analyses of the bacteriocin 21 determinant encoded on the *Enterococcus faecalis* pheromone-responsive conjugative plasmid PPD1. *J Bacteriol* 379:7843–7855). Indeed, recent results suggest that *B. subtilis* produces bacteriocins and that one or more are positively regulated by sigW and negatively regulated by sigX.

In summary, $\sigma^W$, and perhaps other ECF σ factors, plays an important role in the complex microbial communities found in soil, but may not be important in the axenic culture conditions of the laboratory. Thus, one likely function of these ECF σ factors is to defend cells against antimicrobial agents produced by other soil bacteria. The identification of cellular defenses against antimicrobial agents is of tremendous interest to the pharmaceutical industry and the possibility of treating patients with fosfomycin together with a FosB inhibitor could greatly increase the effectiveness of this antimicrobial. Ultimately, this work will provide valuable data for the design and screening of new antibacterial compounds. For example, cell wall-associated teichoic acid is thought to be essential for *B. subtilis* survival (Mauel, C., Young, M., Margot, P. and Karamata, D. (1989) The essential nature of teichoic acids in *Bacillus subtilis* as revealed by insertional mutagenesis. *Mol Gen Genet*, 215:388–94; Pooley, H. M., Abellan, F. X. and Karamata, D. (1991) A conditional-lethal mutant of *Bacillus subtilis* 168 with a thermosensitive glycerol-3-phosphate cytidylyltransferase, an enzyme specific for the synthesis of the major wall teichoic acid. *J Gen Microbiol* 137:921–928) and compounds that inhibit teichoic acid (TA) biosynthesis show promise as antimicrobials. Indeed, tunicamycin may act primarily as a TA inhibitor (Ward, J. B. (1977) Tunicamycin inhibition of bacterial wall polymer synthesis. *FEBS Lett* 78:151–154; Ward, J. B., Wyke, A. W. and Curtis, C. A. (1980) The effect of tunicamycin on wall-polymer synthesis in Bacilli. *Biochem Soc Trans* 8:164–166). Daptomycin is a promising new drug, currently in clinical trials under the auspices of Cubist Pharmaceuticals, that selectively inhibits lipotechoic acid synthesis (Boaretti, M., Canepari, P., Lleo, M. M. and Satta, G. (1993) The activity of daptomycin on *Enterococcus faecium* protoplasts: indirect evidence supporting a novel mode of action on lipoteichoic acid synthesis. *J Antimicrob Chemother* 31:227–35; Canepari, P. and Boaretti, M. (1996) Lipoteichoic acid as a target for antimicrobial action. *Microb Drug Resist* 2:85–89; Canepari, P., Boaretti, M., del Mar Lleo, M. and Satta, G. (1990) Lipoteichoic acid as a new target for activity of antibiotics: mode of action of daptomycin (LY146032). *Antimicrob Agents Chemother* 34:1220–1226). Identification of additional genes involved in these essential cellular processes, which are unique to bacteria, will likely provide novel targets for the development of antimicrobials.

As a result of this work, $P_X$- and $P_W$-reporter fusions are useful in commercial drug screening ventures. The effects of substances on the growth and function of bacteria can be measured by using these promoters in the following manner. These promoters can be operably linked to gene sequences that encode proteins whose transcription can be measured in a variety of ways. By inserting these operably linked fusions into vectors derived from various sources, the resulting expression system can be transferred into host cells that allow transcription of the linked genes. The linked genes can encode a variety of reporter proteins. All of the methods used in these assays can be designed to be high-throughput in nature. By using these methods, putative new antimicrobial agents can be identified.

EXPERIMENT 1

Methods

Growth Conditions. Bacteria were cultured at 37 degrees C. with vigorous shaking in 2×YT (Sambrook et al., 1990) or 4×SG containing 0.2% (w/v) glucose (Huang et al., 1998) unless otherwise indicated. In *E. coli.*, $Amp^r$ resistance was selected by using 100 micrograms of ampicillin per ml. For *B. subtilis*, antibiotics used for selection were erythromycin at 2 micrograms per ml, neomycin at 10 micrograms per ml, spectinomycin at 100 micrograms per ml, and macrolides-lincomycin-streptogramin B ($MLS^r$) with 2 micrograms of erythromycin and 25 micrograms of lincomycin per ml.

Bacterial Host Strains. For recombinant DNA work, *E. coli* Jm2r-[(mcrA⁻B⁻ hsdr⁻ M⁺ recA1Δ (lac-proAB) thi gyrA96 relA1 srl::Tn10 F'(proAB lacZΔ M15)] was used as host.

All B. subtilis strains are derivatives of either JH642 (trpC2 pheA1) or CU1065 (W1 68 trpC2 att SPβ). The sigX::spc (HB7007), sigW::erm (HB4246), sigX sigW (HB7121), sigY::erm (HB4245), and rsiX::pVA29 (HB7013) mutant strains have been described previously (Huang et al., 1997; Huang et al., 1998).

Phenotypic Characterization of sigW Mutant. Sporulation was assessed by comparing viable cell counts (colony-forming units) before and after treatment with chloroform and heating at 80 degrees C. for 30 minutes as described (Deuerling, E., Mogk, A., Richter, C., Purucker, M. and Schumann, W. (1997) The ftsH gene of *Bacillus subtilis* is involved in major cellular processes such as sporulation, stress adaptation and secretion. *Mol Microbiol* 23:921–933). Competence was determined by measuring transformation efficiency with chromosomal DNA containing a selectable antibiotic resistance marker. Secretion was measured both by visualization of secreted proteins by coomassie-stained SDS-PAGE (after precipitation with trichloroacetic acid) and by quantitation with the Bradford protein assay reagent.

Construction of Reporter Fusions. The putative promoter regions were amplified using a forward primer around 20 basepairs upstream from the putative −35 consensus with restriction site HindIII, and a reverse primer approximately 50 basepairs downstream of the start codon with restriction site BamHI (primer sequences are available upon request). Chromosomal DNA of *B. subtilis* CU1065 was amplified using Pfu DNA polymerase from Stratagene and the resulting PCR fragments were purified by a QIAGEN gel purification kit and cloned into pJPM122 (Slack, F. J., Mueller, J. P. and Sonenshein, A. L. (1993) Mutations that relieve nutritional repression of the *Bacillus subtilis* dipeptide permease operon. *J Bacteriol* 175:4605–4614) after restricting with BamHI and HindIII. After transformation into *E. coli* JM2r- with selection for ampicillin resistance, plasmids were recovered for each gene as follows: sigW (pXH23), ydbS (pXH33), yeaA (pXH25), ysdB (pXH29), pbpE (pXH34), ywrE (pXH35), yjoB (pAG78), yteI (pAG910), yknW (pAG1112), yobJ (pAG2829), yfhL (pAG2627), yuaF (pAG2425), yxzE (pAG3435), yvlA (pAG3233), xpaC (pAG3031). For the ydbS gene, we prepared an additional pJPM122 derivative using an upstream PCR primer terminating 204 basepairs upstream of the start codon. The resulting PCR product contains the entire ydbR-ydbS intergenic region and was used to construct a reporter fusion designated ydbs-long (pXH21). The sequence of the promoter region in each plasmid was verified by DNA sequencing.

To recombine the promoter region-cat-lacZ operon fusion into the SPβ prophage, each pJPM122 derivative was purified from a single colony by QIAGEN plasmid miniperparation kit, and linearized by digestion with ScaI and transformed into ZB307A [JH642 SPμc2Δ2::Tn917::pSK10Δ6 (MLS$^r$); (Zuber, P. and Losick, R. (1987) Role of AbrB and SpoOA- and SpoOB-dependent utilization of a sporulation promoter in *Bacillus subtilis*. *J Bacteriol* 169:2223–2230)] with selection for Neo$^r$. The resulting strains, for each cloned promoter region, are: sigW, HB7063; ydbS, HB7032; yeaA, HB7065; yxjI, HB7068; ysdB, HB7069; pbpE, HB7100; yjoB, HB8014; yteI, HB8013; yknW, HB8027; ywrE, HB7105; yobJ, HB8040; yfhL, HB8043; yuaF, HB8050; yxzE, HB8057; yvlA, HB8060; xpaC, HB8063. To transduce each reporter fusion into various genetic backgrounds, SPβ phage lysates were prepared by heat induction and used to transduce recipient strains to Neo$^r$. Recipient strains used for these studies included: wild-type strains CU1065 and JH642, sigX::spc (HB7007), sigW::erm (HB4246), sigX sigW (HB7121), sigY::erm (HB4245), and rsiX::pVA29 (HB7013). For the pbpE gene, we also tested a translational pbpE-lacZ fusion described previously (Popham and Setlow, 1993).

Identification of σ$^W$ Dependent Promoters. The *B. subtilis* genome database (SubtiList; Moszer, I., Glaser, P. and Danchin, A. (1995) SubtiList: a relational database for the *Bacillus subtilis* genome. *Microbiol* 141:261–268) was searched using the "Search Pattern" function for sequences similar to the σ$^W$-dependent promoter preceding the sigW-ybbM operon. For each promoter region studied, expression levels were determined by comparing colony color on sporulation plates containing 2% glucose and X-gal and by β-galactosidase assays (Miller, J. H. (1972) Experiments in Molecular Genetics. Cold Spring Harbor Press, Cold Spring Harbor Laboratory, N.Y., pp 352–255) of cultures grown in 4×SG/glucose medium as described previously (Huang et al., 1998).

Computer Analysis. All predicted protein sequences were compared against the non-redundant protein databases using BLAST 2.0 (Altschul, S. F., Madden, T. L., Schaffer, A. A., Zhang, J., Zhang, Z., Miller, W. and Lipman, D. J. (1997) Gapped BLAST and PSI-BLAST: a new generation of protein database search programs. *Nucleic Acids Res* 25:3389–3402). Protein searches against the *B. subtilis* genome used either BLAST or FASTA programs as available on the SubtiList web site (Moszer, et al., 1995). Protein localization was predicted using both the PSORT (Nakai, K. and Kanehisa, M. (1991) Expert system for predicting protein localization sites in Gram-negative bacteria. *PROTEINS: Structure, Function, and Genetics* 11:95–110) and TMPred (Hofmann, K. and Stoffel, W. (1993) TMbase—A database of membrane spanning proteins segments. *Biol Chem Hoppe-Seyler* 347:166)

RNA and Transcription Analyses. Run off transcription assays were performed as described (Huang et al., 1998) using promoter fragments amplified by the PCR from pJPM122 subclones that had been tested for in vivo expression activity and verified by DNA sequencing. RNA isolation and primer extension mapping of in vivo start sites were performed as described (Huang and Helmann, 1998).

EXAMPLE 2

Identification of Candidate σ$^W$-Dependent Promoters

The *B. subtilis* genome was searched for sequences similar to P$_w$. Altogether, there are 27 perfect matches to the 10 base pair sequence SEQ ID NO: 1. Of these 27 sites, 16 are positioned such that transcription would initiate between 13 and 53 bases upstream of the start codon of the corresponding gene (FIG. 2). The remaining 11 matches are not appropriately positioned to function as promoter elements and are probably chance occurrences, although they might control unrecognized genes or regulatory RNAs.

EXAMPLE 3

In Vitro Activity of σ$^W$-Dependent Promoters

Each putative promoter region was amplified by PCR using primers located approximately 20 basepairs upstream of the putative −35 region and 50 basepairs downstream of the start codon for the corresponding gene. In all cases, reconstituted Eσ$^W$ was active with the resulting templates and produced a run-off transcript of the expected size. Representative results are shown in FIG. 4.

In nearly every case, RNA polymerase lacking added $v^W$ did not produce a run-off product. The sole exception is yknW. It is possible that yknW can also be recognized by a σ factor contaminating our RNA polymerase core preparation.

With the yeaA template a ladder of transcripts differing in length by a single nucleotide is produced. A similar pattern is seen in vivo (see below). Since the initial transcribed region of yeaA has the sequence 5'-AAAAAC-3', it appears that these larger transcripts arise by reiterative (slippage) synthesis during initiation (Uptain, S. M., Kane, C. M. and Chamberlin, M. J. (1997) Basic mechanisms of transcript elongation and its regulation. *Ann Rev Biochem* 66:117–172).

EXAMPLE 4

In Vivo Activity of $\sigma^W$-Dependent Promoters

To determine if these promoters are active and dependent on $\sigma^W$ in vivo, lacZ reporter fusions in prophage SPβ were constructed. In most cases, expression is completely dependent on $\sigma^W$ as measured during growth on plates (FIG. 5). This is confirmed in liquid culture assays where expression levels in the sigW mutant are typically at or near background (0.5 to 1 Miller unit). The most notable exceptions are yknW (consistent with the in vitro transcription results, FIG. 4) and xpaC. The activity of the yknW promoter region is reduced to the background level in a sigX sigW double mutant, indicating that $E\sigma^W$ may also recognize this site at a low level. The only promoter that does not clearly belong to the $\sigma^W$ regulon is the weak element preceding the xpaC operon. Therefore, cloned promoter elements are, for the most part, only recognized by $\sigma^W$ in vivo.

As noted previously for the sigW autoregulatory promoter (Huang et al., 1998), in all cases tested, gene expression was increased in a sigX mutant and decreased in an rsiX mutant (FIG. 5). This confirms the previous observation that the $\sigma^W$ and $\sigma^W$ regulons are mutually antagonistic, i.e. a decrease in sigX activity leads to increased expression of $\sigma^W$-dependent genes. Conversely, an increase in $\sigma^X$ activity, due to mutation of the negative regulator rsiX (Brutsche, S. and Braun, V. (1997) SigX of *Bacillus subtilis* replaces the ECF sigma factor FecI of *Escherichia coli* and is inhibited by RsiX. *Molecular & General Genetics* 256:416–425; Huang et al, 1997), decreases $\sigma^W$-dependent expression. In contrast, mutation of another ECF σ factor, $\sigma^Y$, has little effect on most $\sigma^W$ controlled genes. The one striking exception is yjoB. Expression of the yjoB-cat-lacZ transcriptional fusion is increased 2-fold in a sigY mutant as determined in liquid culture assays.

EXAMPLE 5

Growth Phase Dependence of Gene Expression

Figure 6:
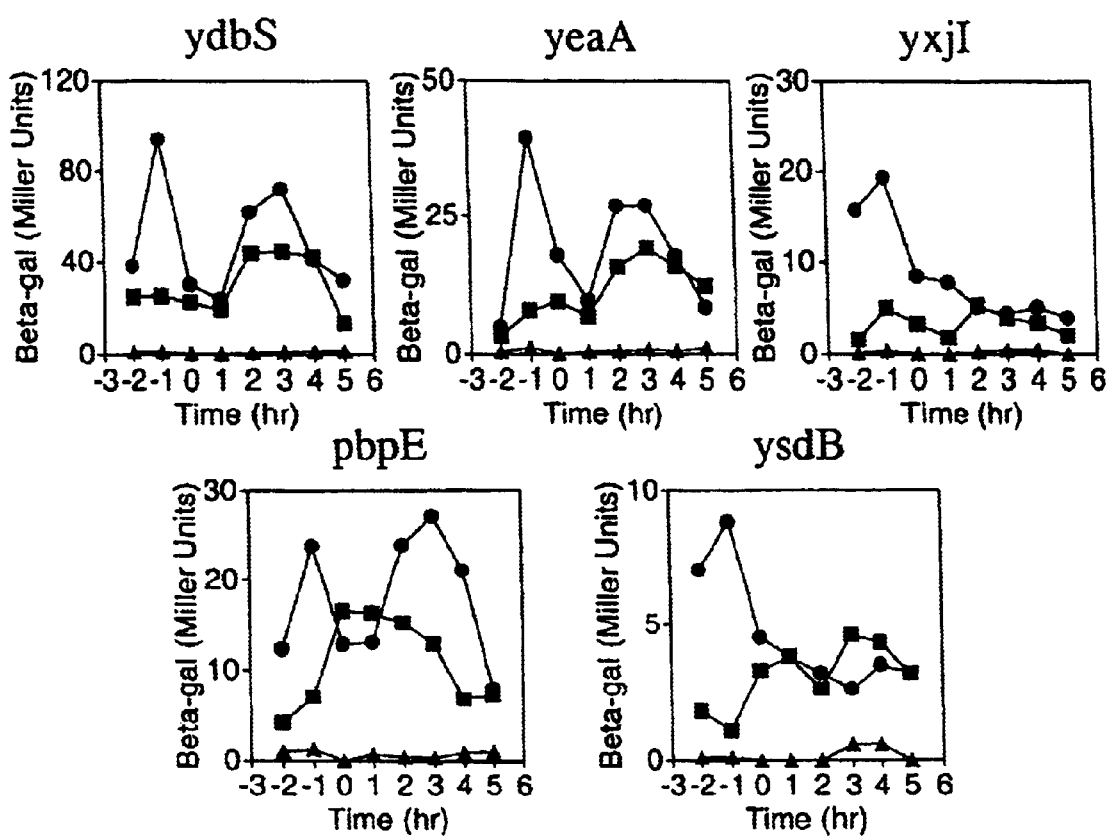
FIG. 6 shows the in vivo expression of five representative $\sigma^W$-dependent promoters. The indicated promoter regions were cloned as cat-lacZ operon fusions and integrated in SPβ. The expression level (in Miller units) is indicated for fusions in the wild-type (filled squares), sigW (filled diamonds), and sigX (filled circles) mutant backgrounds. Growth phase is indicated in hours relative to the end of logarithmic phase growth (defined at $T_0$).

A detailed analysis of the growth phase dependence of gene expression for five representative promoters of the $\sigma^W$ regulon was performed. In general, the timing and pattern of expression is similar to that reported previously for sigX (Huang et al., 1998) and pbpE (Popham and Setlow, 1993) in that expression is weak during vegetative growth and increases upon entry into the stationary phase (FIG. 6). In the sigX mutant strain, expression from each promoter is increased two- to ten-fold in late logarithmic phase growth ($T_{-1}$), a time when $\sigma^X$-dependent genes are optimally expressed (Huang et al., 1997; Huang and Helmann, 1998). This leads to an interesting biphasic pattern of expression in the sigX mutant. There is a peak of expression during late logarithmic phase when $\sigma^X$ would normally be active, and then a second peak three to four hours later during early stationary phase, when $\sigma^W$ activity is normally greatest. It is possible that the sigX mutation might increase the activity of some σ factor other than $\sigma^W$ that might account for the first peak of transcription in late logarithmic phase cells; however, for all five genes tested, expression is eliminated in a sigX sigW double mutant. Therefore, both peaks of expression are dependent on $\sigma^W$.

EXAMPLE 6

Mapping of $\sigma^W$-Dependent Start Sites In Vivo

Figure 7:
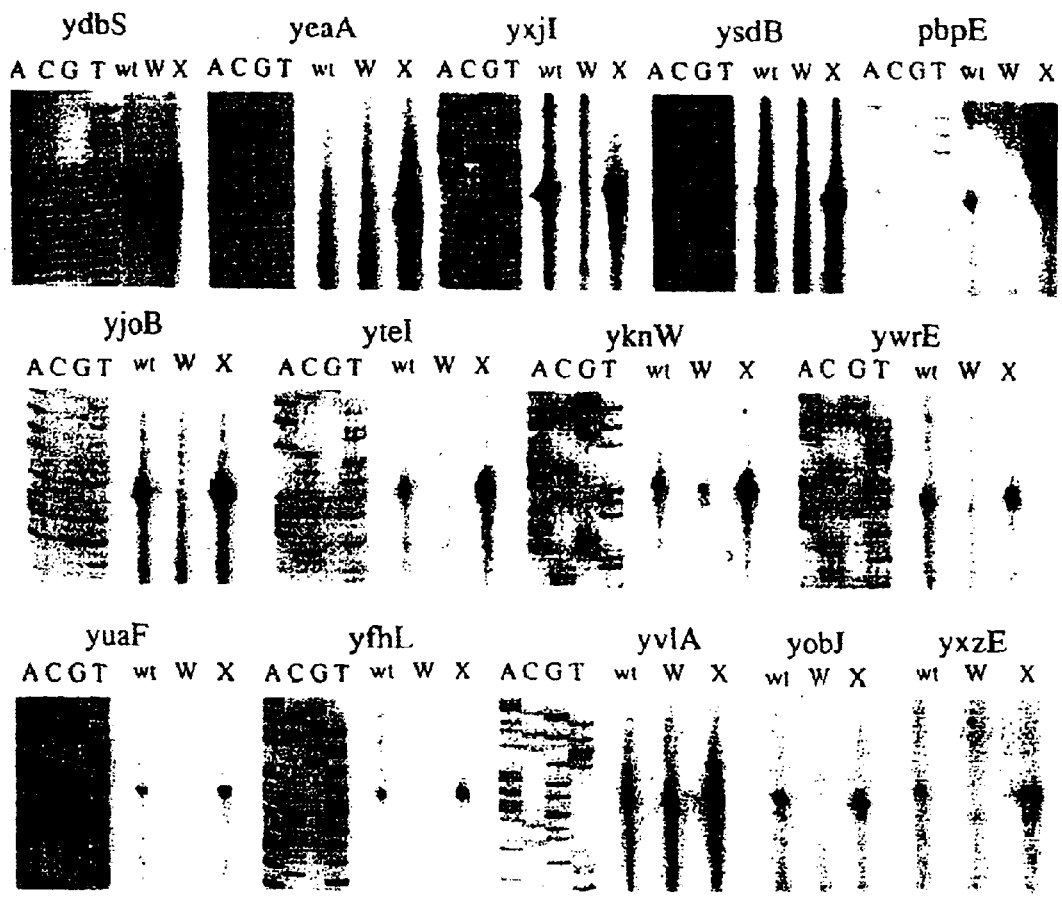
FIG. 7 shows primer extension mapping of $\sigma^W$-dependent promoter elements. RNA was isolated from late logarithmic phase cells of the wild-type (wt) or sigW (W) or sigW (X) mutant strains as described (Huang and Helmann, 1998). Primer extension products, generated using a reverse primer that anneals in the +50 region of the indicated gene, were electrophoresed adjacent to a sequencing ladder generated using the same primer (except for yviA, yobJ, and yxzE where the products were sized relative to a different sequencing ladder). Transcription start sites deduced from this data are summarized in FIG. 2.

Reverse transcriptase primer extension mapping was used to localize the $\sigma^W$-dependent transcription start sites (FIG. 7, summarized in FIG. 2). With the exceptions of xpaC and yeaA, transcripts were detected from each predicted $\sigma^W$ promoter in RNA from wild-type cells. In the case of yeaA, the corresponding transcripts were readily detected in RNA from the sigX mutant. As expected, the $\sigma^W$-dependent transcripts were absent from the sigW mutant cells. The exception is a faint transcript still present from the yknW promoter (FIG. 7), consistent with the ability of this element to be recognized in vitro by RNA polymerase lacking $\sigma^W$ activity (FIG. 4). In corroboration of the plate phenotypes (FIG. 5), the $\sigma^W$-dependent transcripts are more abundant in RNA prepared from the sigX mutant strain.

All of the in vivo start sites are 8 to 10 basepairs downstream of the CGTA −10 element (FIG. 2). The one apparent exception, yeaA, may be an anomaly. As noted in the run-off transcription experiments (FIG. 4), the initial transcribed region of this gene appears to induce slippage synthesis. The in vivo primer extension data indicates that slippage synthesis also occurs at this site in vivo.

EXAMPLE 7

Contribution of Other Promoters to Expression of the $\sigma^W$ Regulon

Since the cloned promoter fragments only include 80 to 100 basepairs of DNA upstream of the start codon, the possibility that the presence of upstream promoters contributes to in vivo expression cannot be excluded. This possibility was investigated in several ways.

First, the sigW-dependence of pbpE expression was compared when cloned at SPβ with a previously described lacZ translational fusion integrated at the pbpE locus (Popham and Setlow, 1993). Unlike the transcriptional fusion at SPβ, the translational fusion retained significant expression in the sigW mutant (92 vs. 21 Miller units in the wild type and sigW mutant, respectively). The residual expression detected in a sigW mutant when at the chromosomal locus is abolished in a sigX sigW double mutant, suggesting that pbpE, like yknW, is part of both the $\sigma^X$ and $\sigma^W$ regulons. Despite the differences in expression for the translational fusion (at the pbpE locus) and the transcriptional fusion (at SPβ; FIG. 2), it seems clear that pbpE depends primarily on $\sigma^W$ for expression in vivo.

Second, the expression of the ydbS promoter region was compared when cloned on a short fragment extending 17 basepairs upstream of the −35 consensus (78 basepairs of non-coding DNA) with a longer fragment containing the entire ydbR-ydbS intergenic region (230 basepairs of non-coding DNA). In both cases, the level of expression was similar and was largely $\sigma^W$-dependent. However, with the longer fragment there was a very low level of expression in a sigW mutant as judged by barely detectable expression on plates, compared to no detectable expression with the shorter fragment. However, no primer extension product corresponding to this element could be identified, and this additional promoter, if present, is of questionable relevance.

Third, all reverse transcriptase mapping experiments were examined for the presence of signals that might indicate additional promoters. In no case was an upstream promoter comparable in strength to the $\sigma^W$-dependent site identifies. For four genes (ysdB, yvlA, yuaF, and yknW), no upstream signals are detected. In several other cases, very weak upstream signals are detected. Analysis of these signals identifies a possible $\sigma^A$-type promoter initiating transcription 117 basepairs upstream of yteI, and several weak signals upstream of yjoB.

Some genes of the $\sigma^W$ regulon may be part of complex operons and therefore expressed, albeit weakly, as part of longer transcripts. In three cases (ywrE, yobJ, and yxzE), there are multiple, diffuse signals throughout the upstream region suggesting that RNA may extend into these genes from upstream genes. A similar conclusion is reached from analysis of the yxjI, yfhL, ydbS, and yeaA genes. In these four cases, a very clear but weak upstream signal maps to the base of the stem-loop of a putative rho-independent terminator for an upstream gene. These signals presumably arise from reverse transcriptase pausing at the base of the G-C rich terminator hairpin and imply that some RNA extends through the terminator into the downstream gene. The biological relevance of this finding is not clear: it may merely reflect the high sensitivity of the primer extension assay and the fact that terminators are not 100% efficient. It is interesting to note that the ydbST operon is downstream of genes encoding D-ala-D-ala ligase (ddlA), the D-ala-D-ala adding enzyme (murF), and a putative RNA helicase (ydbR). There is also a possible $\sigma^W$-type promoter in the end of the murF gene that could contribute to some of the observed readthrough transcription.

In summary, this analysis suggests that the representative genes of the $\sigma^W$ regulon that have been identified are likely to be largely, if not exclusively, dependent on $\sigma^W$ for their in vivo expression. This predicts that a sigW mutant strain will fail to express the various proteins identified as members of the $\sigma^W$ regulon. This contrasts with the previous analysis of the $\sigma^X$ regulon. In that case, most $\sigma^X$-dependent genes have complex promoter regions recognized by multiple holoenzymes (Huang and Helmann, 1998).

EXAMPLE 8

Phenotype of the sigW Mutant

Identification of members of the $\sigma^W$ regulon allows prediction of the phenotypes likely to be associated with a sigW mutation. A sigW mutant strain is not grossly defective in any of the well-characterized processes associated with post-exponential phase, including sporulation, competence, and protein secretion. It has been previously reported that sigW transcription is not induced by a temperature shift from 37 to 50 degrees C. (Huang et al., 1998) and the same is true for the four tested members of the $\sigma^W$ regulon (ydbS, yeaA, yxjI, ysdB). Since several members of the $\sigma^W$ regulon encode enzymes with a predicted detoxification function (FIG. 3), a sigW mutant was tested for increased sensitivity to a variety of chemical insults. However, no differences were apparent in the zones of inhibition produced by HCl, NAOH, NaCl, EDTA, dithiothreitol, 2-mercaptoethanol, lysozyme, sodium dodecyl sulfate, hydrogen peroxide, methyl viologen, metal ions ($Mn^{2+}$ or $Fe^{3+}$), or antibiotics (spectinomycin, ampicillin, chloramphenicol, neomycin, bacitracin, polymyxins, nisin, tetracycline, or gentamicin sulfate).

It will now be apparent to those skilled in the art that other embodiments, improvements, details, and uses can be made consistent with the letter and spirit of the foregoing disclosure and within the scope of this patent, which is limited only by the following claims, construed in accordance with the patent law, including the doctrine of equivalents.

What is claimed is:

1. A deoxyribonucleic acid sequence consisting of SEQ ID NO: 1.

2. The deoxyribonucleic acid sequence of claim 1 comprising a gene promoter.

3. A fusion construct comprising the deoxyribonucleic acid sequence of claim 2, operably linked to a second deoxyribonucleic acid sequence.

4. The fusion construct of claim 3, wherein the second deoxyribonucleic acid sequence encodes a reporter protein.

5. An expression vector comprising the fusion construct of claim 3.

6. The expression vector of claim 5 wherein said expression vector is inserted into a host cell that allows transcription of the fusion construct contained in the expression vector.

* * * * *